United States Patent [19]

Hirschberg

[11] Patent Number: 4,573,480
[45] Date of Patent: Mar. 4, 1986

[54] IMPLANTABLE ELECTRODE LEAD WITH MICROPOROUS INSULATION

[75] Inventor: Jakub Hirschberg, Täby, Sweden

[73] Assignee: Siemens Aktiengesellschaft, Berlin & Munich, Fed. Rep. of Germany

[21] Appl. No.: 562,756

[22] Filed: Dec. 19, 1983

[30] Foreign Application Priority Data

Feb. 16, 1983 [DE] Fed. Rep. of Germany ....... 3305271

[51] Int. Cl.⁴ .............................................. A61N 1/04
[52] U.S. Cl. ................ 128/784; 128/419 P; 128/DIG. 14
[58] Field of Search ............... 128/419 P, 639, 642, 128/784, 785, 786, DIG. 14

[56] References Cited

U.S. PATENT DOCUMENTS

| | | | |
|---|---|---|---|
| 3,035,583 | 5/1962 | Hirsch | 128/DIG. 14 |
| 4,033,355 | 7/1977 | Amundson | 128/786 |
| 4,082,893 | 4/1978 | Okita | 128/DIG. 14 |
| 4,269,198 | 5/1981 | Stokes | 128/785 |
| 4,301,815 | 11/1981 | Doring | 128/786 |
| 4,407,303 | 10/1983 | Akerstrom | 128/786 |

FOREIGN PATENT DOCUMENTS

WO80/48010 10/1980 PCT Int'l Appl. ................ 128/786

OTHER PUBLICATIONS

Shanti Mehta, "A Statistical Summary of the Results of Femoro-Popliteal Bypass Surgery", Apr. 1979.

*Primary Examiner*—William E. Kamm
*Attorney, Agent, or Firm*—John Francis Moran

[57] ABSTRACT

Electrode configuration for use in medical applications, in particular for implantable cardiac pacemakers, includes a porous synthetic material, in particular porous polyfluoroethylene which is used as insulation for the wiring associated with the electrode. The pore size should be 4 μm or less. It is preferable to sinter the surface to a non-porous, smooth layer.

14 Claims, 1 Drawing Figure

U.S. Patent  Mar. 4, 1986  4,573,480
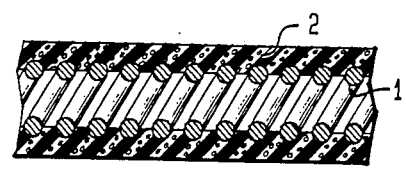

IMPLANTABLE ELECTRODE LEAD WITH MICROPOROUS INSULATION

BACKGROUND OF THE INVENTION

This invention is related to an electrode for use in medical applications, in particular, for an implantable cardiac pacemaker, with an insulated wiring system and at least one electrode for electrical contact with body tissue.

Electrodes of this kind have been generally known for a long time. Examples include unipolar or bipolar electrodes for cardiac stimulation with mono- or multifilar wiring and a great variety of electrodes. A common insulating material is silicon rubber. The silicon rubber meets quite well the requirement of high flexibility, long mechanical life and bodily compatibility that are imposed on the insulation. However, it also tends to expand slightly over the length of the electrode, which can lead to difficulties, particularly in the case of insertion by means of a mandrin, and also when circumstances necessitate removal from the body. In addition, the surface of this insulation is not as smooth as would be desirable for friction-free insertion through the veins and for movement within the veins.

For this reason, a number of experiments have been conducted, to replace silicon rubber with other synthetic materials. Tests with polyurethane have indeed confirmed its good mechanical properties, but there is controversy with regard to its chemical behavior, that is, its reaction to body fluids.

Similarly, polyethylene has not so far been able to offer any improvement. This material appears to be weaker than silicon rubber when exposed to enduring mechanical loads, and is also not quite as flexible.

SUMMARY OF THE INVENTION

It is an object of the present invention to provide an insulating material for electrodes of the type referred to above which meet the high standards required in medicine and which offer advantages over presently known electrodes.

According to the invention, there is provided a porous synthetic material, in particular, porous polytetrafluoroethylene, as an insulating material for the wire(s). This material combines all the necessary properties in an outstanding manner. It has great durability, it is very flexible as a result of its pores, it displays excellent biocompatibility, has an extremely smooth surface, hardly expands at all in a lengthwise direction and is resistant to all body fluids. In addition, it can withstand considerably higher temperatures than the familiar materials, so that sterilization, too, is facilitated.

In preferred embodiments, the pore sizes measure 4 $\mu$m or less and the insulation comprises layers of varying porosity.

In further embodiments, the porous synthetic material is at least partially covered with a smooth and impervious layer. The smooth layer may be obtained by centering the outer parts of the porous material. Also, additional material may be added which projects away from the insulation in such a manner as to form means for anchoring the electrode configuration.

Other features and advantages of the invention will be apparent from the following description of the preferred embodiments and from the claims.

BRIEF DESCRIPTION OF THE DRAWING

The sole FIGURE shows a cross-sectional view of an electrode lead.

For a full understanding of the present invention, reference should now be made to the following detailed description of the preferred embodiments of the invention.

DETAILED DESCRIPTION

Porous polytetrafluoroethylene has been known for many years as a desirable material for blood vessel prosthesis (A Statistical Summary of the Results of Femoro-Popliteal Bypass Surgery, Technical Note Number 175, April 1979). Nevertheless, the use of this material for insulation for implantable electrode configurations has eluded previous investigators. Normal polytetrafluoroethylene is much too stiff and therefore completely unsuitable for this purpose. The familiar blood vessel prostheses are not perfectly sealed, due to the size of their pores, and they permit tissue to grow on the outside, which prevents friction-free sliding or movement.

However, by skillful optimization of the porosity of the material a plastic with the desired insulating properties could be obtained. The size of the pores must be selected so that the insulation has a high flexibility yet is nevertheless sufficiently impervious to body fluid.

In a preferred embodiment of the invention it is specified that the pore size shall be 4 $\mu$m or less.

A particularly useful insulation is obtained by manufacturing the insulation out of layers of different porosity, with the pore size for at least one layer being so small that the layer in question is absolutely impervious. It is still more advantageous to have this layer as the outermost layer, since by this means it is possible simultaneously to obtain the smoothest surface. The small pore size on the surface also permanently prevents tissue from growing into the insulation or around it so that the good sliding characteristics are maintained.

As a further improvement, or, alternatively, instead of using different layers, the porous plastic can be covered on at least part of its outer surface with a smooth and impervious layer. This layer can be obtained by sintering the outer sections of the porous plastic.

A further preferred embodiment provides that the insulation shall have areas of varying porosity along its length. Thus, for example, in the vicinity of the electrode(s), areas with large pores serve to insure that this part of the electrode configuration will grow in after the implantation. In this way, dislocations can be prevented simply and securely. The areas with large pores can be produced, for example, by the additional application of plastic. A simple solution to the manufacturing problem in this connection is to apply a ring of macroporous plastic.

In order to permit immediate anchorage when the implantation takes place, it is particularly advantageous if the added plastic forms, at least in some areas, project from the insulation in such a way that they form a means of anchoring. In the vicinity of the electrodes, for example, flexible barbs pointing away from the electrodes themselves may be provided.

The invention is described and explained in greater detail below, by way of an example and an actual embodiment. The embodiment is based on a unipolar configuration of electrodes for cardiac stimulation, which consists of an extended, helical electrical conductor, which is provided at the distal end with an electrode, which may be of platinum or glass carbon and is designed for the transmission of stimulation pulses and/or the detection of cardiac activity, and in which the conductor is surrounded with an insulating sheath made of porous polytetrafluoroethylene. The wall of this insulation sheath is 0.4 mm thick. The pores have an average size of 4 μm. The surface of the insulating sheath is fused by sintering into a closed, non-porous and extremely smooth layer. Due to the good properties of this material, the thickness of the insulating sheath can be smaller than when, for example, silicone rubber is used, so that the overall diameter of the electrode configuration can be reduced.

In the sole FIGURE, a conductor 1 of wire-shaped material is wound into a spiral to promote flexibility. Also, other suitable conductors may be in the form tape-like material, multifilar wound conductors, or coaxially wound conductors. Conductor 1 is encapsulated by an insulating sleeve 2 of porous synthetic material which in this case is polytetrafluoroethylene. It should be noted that the pores are exaggerated in size for illustration purposes. A suitable pore size in this case may measure approximately three micrometers in diameter size.

In the vicinity of the electrode, distributed around the circumference of the insulating sheath, there have also been added a number of finlike, macroporous polytetrafluoroethylene pieces that project away from the electrode and the insulation, into which fibrous tissue can grow after the implantation.

There has thus been shown and described a novel insulation for implantable electrodes which fulfills all the objects and advantages sought therefor. Many changes, modifications, variations and other uses and applications of the subject invention will, however, become apparent to those skilled in the art after considering the specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. An implantable electrode lead of the type having an electrode tip for coupling an electrical stimulator with body tissue to be stimulated through the electrode tip, the implantable electrode lead comprising: a generally helically wound electrical conductor; at least one flexible, cylindrical insulating sleeve for coaxially encapsulating the electrical conductor to provide an insulator; and the insulating sleeve comprises a porous synthetic material that is polytetrafluoroethylene having a predetermined pore size that makes the insulating sleeve highly flexible and bendable while being essentially impervious to body fluids to prevent tissue growth thereon.

2. An implantable electrode according to claim 1, wherein the pore size of said insulation is not larger than 4 μm.

3. An implantable electrode according to claim 2, wherein said porous synthetic material on the outside of the said insulation is at least partially covered with a smooth impervious layer.

4. An implantable electrode according to claim 1, wherein said insulator comprises layers of varying porosity, with the pore size in at least one layer being so small that the layer is impervious to body fluids.

5. An implantable electrode according to claim 1, wherein said porous synthetic material on the outside of said insulator is at least partially covered with a smooth and impervious layer.

6. An implantable electrode according to claim 5, wherein said smooth layer is formed out of the outer portion of said porous synthetic material by heating same.

7. An implantable electrode according to claim 1, wherein said insulator is of varying porosity in its outer section along said electrode configuration.

8. An implantable electrode according to claim 7, wherein said smooth layer is formed out of the outer portion of said porous synthetic material by sintering.

9. An implantable electrode according to claim 8, wherein said additional synthetic material includes portions that project away from said insulation in such a manner as to form a means of anchoring.

10. An implantable electrode according to clam 1, further comprising additional synthetic material with a larger pore size applied to said insulation.

11. An implantable electrode according to claim 10, wherein said additional synthetic material is applied in the form of a ring.

12. Electrode configuration according to claim 11, wherein said additional synthetic material at least in some cases forms areas that project away from said insulation in such a manner as to form a means of anchoring.

13. An implantable electrode according to claim 10, wherein said additional synthetic material at least in some cases has portions that project away from said insulation in such a manner as to form a means of anchoring.

14. Electrode configuration according to claim 13, wherein said additional synthetic material at least in some cases forms areas that project away from said insulation in such a manner as to form a means of anchoring.

* * * * *